United States Patent
Edwards et al.

(10) Patent No.: US 6,562,059 B2
(45) Date of Patent: May 13, 2003

(54) VASCULAR SEALING DEVICE WITH MICROWAVE ANTENNA

(75) Inventors: Stuart D. Edwards, Portola Valley, CA (US); Ronald Lax, Palm City, FL (US); Theodore L. Parker, Danville, CA (US); Thomas C. Wehman, Cupertino, CA (US); Theodore Kucklick, Los Gatos, CA (US); Eugene Skalnyi, Mountain View, CA (US)

(73) Assignee: NeoMend, Inc., Sunnyvale, CA (US)

( * ) Notice: Subject to any disclaimer, the term of this patent is extended or adjusted under 35 U.S.C. 154(b) by 0 days.

(21) Appl. No.: 10/132,848

(22) Filed: Apr. 23, 2002

(65) Prior Publication Data

US 2002/0165528 A1 Nov. 7, 2002

Related U.S. Application Data

(60) Division of application No. 09/334,300, filed on Jun. 16, 1999, now abandoned, which is a continuation of application No. 08/963,408, filed on Nov. 3, 1997, now Pat. No. 6,033,401, which is a continuation-in-part of application No. 08/963,033, filed on Nov. 3, 1997, now abandoned, which is a continuation-in-part of application No. 08/963,082, filed on Nov. 3, 1997, now abandoned.
(60) Provisional application No. 60/036,299, filed on Mar. 12, 1997.

(51) Int. Cl.$^7$ ............................................. A61B 17/08
(52) U.S. Cl. ..................................................... 606/213
(58) Field of Search ........................... 406/1, 213–215; 604/82, 83, 502, 506, 508

(56) References Cited

U.S. PATENT DOCUMENTS

| | | |
|---|---|---|
| 4,424,833 A | 1/1984 | Spector et al. |
| 4,555,242 A | 11/1985 | Saudagar |

(List continued on next page.)

FOREIGN PATENT DOCUMENTS

| | | |
|---|---|---|
| EP | 0 330 344 | 2/1988 |
| EP | 0 476 178 A1 | 3/1992 |

(List continued on next page.)

OTHER PUBLICATIONS

Abergelm R.P. et al., "Skin Closure by Nd:YAG Laser Welding" American Academy of Dermatology 1986 14(5):810–14.

Anand, R.K. et al., "Laser Balloon Angioplasty: Effect of Constant Temperature Versus Constant Power on Tissue Weld Strength" Lasers in Surgery and Medicine 1988 8(1):40–44.

(List continued on next page.)

*Primary Examiner*—Michael Peffley
(74) *Attorney, Agent, or Firm*—Ryan Kromholz & Manion, S.C.

(57) ABSTRACT

A device and method are provided for sealing a puncture in a body vessel. The device has an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; and a microwave antenna for delivering microwave energy adjacent the distal end of the elongated body to the fluent closure compound precursor. The microwave antenna according to this embodiment is preferably incorporated onto the elongated body adjacent the body distal end. Alternatively, the device can include a guidewire lumen and a guidewire which includes a microwave antenna.

6 Claims, 19 Drawing Sheets

U.S. PATENT DOCUMENTS

| | | |
|---|---|---|
| 4,738,658 A | 4/1988 | Magro et al. |
| 4,744,364 A | 5/1988 | Kensey |
| 4,838,280 A | 6/1989 | Haaga |
| 4,852,568 A | 8/1989 | Kensey |
| 4,874,368 A | 10/1989 | Miller et al. |
| 4,890,612 A | 1/1990 | Kensey |
| 4,891,359 A | 1/1990 | Saferstein et al. |
| 5,002,051 A | 3/1991 | Dew et al. |
| 5,021,059 A | 6/1991 | Kensey et al. |
| 5,041,129 A | 8/1991 | Hayhurst et al. |
| 5,042,985 A | 8/1991 | Elliott et al. |
| 5,053,046 A | 10/1991 | Janese |
| 5,061,274 A | 10/1991 | Kensey |
| 5,108,421 A | 4/1992 | Fowler |
| 5,129,882 A | 7/1992 | Weldon et al. |
| 5,156,613 A | 10/1992 | Sawyer |
| 5,159,937 A | 11/1992 | Tremulis |
| 5,163,906 A | 11/1992 | Ahmadi |
| 5,171,222 A | 12/1992 | Euteneuer et al. |
| 5,192,300 A | 3/1993 | Fowler |
| 5,197,971 A | 3/1993 | Bonutti |
| 5,221,259 A | 6/1993 | Weldon et al. |
| 5,222,974 A | 6/1993 | Kensey et al. |
| 5,250,025 A | 10/1993 | Sosnowski et al. |
| 5,275,616 A | 1/1994 | Fowler |
| 5,281,197 A | 1/1994 | Arias et al. |
| 5,282,827 A | 2/1994 | Kensey et al. |
| 5,290,310 A | 3/1994 | Makower et al. |
| 5,292,309 A | 3/1994 | Van Tassel et al. |
| 5,292,332 A | 3/1994 | Lee |
| 5,306,254 A | 4/1994 | Nash et al. |
| 5,324,306 A | 6/1994 | Makower et al. |
| 5,330,518 A | 7/1994 | Neilson et al. |
| 5,344,435 A | 9/1994 | Turner et al. |
| 5,383,896 A | 1/1995 | Gershony et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,292 A | 8/1995 | Kipshidze et al. |
| 5,441,517 A | 8/1995 | Kensey et al. |
| 5,447,502 A | 9/1995 | Haaga |
| 5,486,195 A | 1/1996 | Myers et al. |
| 5,496,332 A | 3/1996 | Sierra et al. |
| 5,507,744 A | 4/1996 | Tay et al. |
| 5,571,216 A | 11/1996 | Anderson |
| 5,575,815 A | 11/1996 | Slepian et al. |
| 5,591,204 A | 1/1997 | Janzen et al. |
| 5,591,205 A | 1/1997 | Fowler |
| 5,601,602 A | 2/1997 | Fowler |
| 5,612,050 A | 3/1997 | Rowe et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag |
| 5,665,106 A | 9/1997 | Hammerslag |
| 5,665,107 A | 9/1997 | Hammerslag |
| 5,669,934 A | 9/1997 | Sawyer |
| 5,676,689 A | 10/1997 | Kensey et al. |
| 5,700,273 A | 12/1997 | Buelna et al. |
| 5,725,498 A | 3/1998 | Janzen et al. |
| 5,725,551 A | 3/1998 | Myers et al. |
| 5,728,132 A | 3/1998 | Van Tassel et al. |
| 5,810,885 A * | 9/1998 | Zinger .................... 606/213 |
| 5,814,066 A * | 9/1998 | Spotnitz .................. 606/214 |
| 5,895,412 A | 4/1999 | Tucker |
| 5,954,715 A | 9/1999 | Harrington et al. |
| 6,033,401 A * | 3/2000 | Edwards et al. ............. 606/41 |
| 6,159,232 A * | 12/2000 | Nowakowski ............. 606/213 |
| 6,179,862 B1 * | 1/2001 | Sawhney .................. 606/214 |

FOREIGN PATENT DOCUMENTS

| | | |
|---|---|---|
| EP | 0 482 350 A2 | 4/1992 |
| EP | 0 482 350 B1 | 12/1996 |
| GB | 1 569 660 | 7/1977 |
| WO | 91/09641 | 7/1991 |
| WO | 92/22252 | 12/1992 |

OTHER PUBLICATIONS

Chuck, R.S. et al., "Dye–Enhanced Laser Tissue Welding", Lasers in Surgery and Medicine 1989 9(5): 471–477.

DeCoste, S.D. et al., "Dye–Enhanced Laser Welding for Skin Closure", Lasers in Surgery and Medicine 1992 12:25–32.

Fujitani, R.M. et al., "Biophysical Mechanisms of Argon Laser–Assisted Vascular Anastomoses", Current Surgery, Mar.–Apr. 1998, 119–123.

Goldstein, J.D. et al., "Development of a Reconstituted Collagen Tendon Prophesis", The Journal of Bone and Joint Surgery, 1998 71–A(8): 1183–91.

Grubbs, P.E. et al., "Enhancement of CO2 Laser Microvascular Anastomoses by Fibrin Glue", Journal of Surgical Research 1988 45:112–119.

Grubbs, P.E. et al, "Determinants of Weld Strength in Laser–Assisted Microvascular Anastomosis", Current Surgery Jan.–Feb. 1989 pp. 3–5.

Jain, K..K. et al., "Repair of Small Blood Vessels with Neodymium–YAG Laser: A Preliminary Report", Surgery 85(6):684–8.

Kopchok, G. et al., "Thermal Studies of In Vivo Vascular Tissue Fusion by Argon Laser", Journal of Investigative Surgery, 1988 1:5–12.

Kopchok, G. et al., "Argon Laser Vascular Welding" The Thermal Component SPIE, 1986 712:260–3.

Kopchock, G. et al., "CO2 and Argon Laser Vascular Welding: Acute Histologic and Thermodynamic Comparison", Lasers in Surgery and Medicine, 1988 8:584–8.

Lemole, G.M. et al., "Preliminary Evaluation of Collagen as a Component in the Thermally–induced 'Weld'", SPIE, 1991, 1422:116–22.

Miniberg, D.T. et al., "Laser Welding of Perdicled Flap Skin Tubes," The Journal of Urology, 1989, 142(2):623–5.

Nimni, M.E. "Third International Congress of Biorhology Symposium on the Soft Tissues Around a Diarthodial Joint", Biorthology, 19810 17:51–82.

Oz, M.C. et al., "Tissue Soldering By Use of Indocyanine Green Dye–Enhanced Fibrinogen with the Near Infrared Diode Laser", Journal of Vascular Surgery, 1990 11(5):718–25.

Oz, M.C. et al., "In Vitro Comparison of Thulium–Holmium–Chromium–YAG and Argon Ion Laser fo r Welding of Biliary Tissue", Lasers in Surgery and Medicine, 1989 9:42–44.

Poppas, D.P. et al., "Laser Welding in Urethral Surgery: Improved Results with a Protein Solder", The Journal of Urology, 1988, 139:415–17.

Schober, R. et al., "Laser–Induced Alteration of Collagen Substructure Allows Microsurgical Tissue Welding", Science, Jun. 1986 232:1421–2.

Murray, L.W. et al., "Crosslinking of Extracellular Matrix Proteins", Lasers in Surgery and Medicine, 1989, 9:490–6.

Tanzer, M.L. et al., "Cross–Linking of Collagen", Science, 180:561–6.

Vale, B.H. et al., "Microsurgical Anastomosis of Rat Carotid Arteries with the CO2 Laser", Plastic and Reconstructive Surgery 77(5):759–66.

White, R.A. et al., "Argon Laser—Welded Arteriovenous Anastomoses", Journal of Vascular Surgery, 1987 6(5):447–53.

White, R.A. et al., "Comparison of Laser–Welded and Sutured Arteriotomies", Arch. Surg. 1986, 121:1133–5.

White, R.A. et al, "Mechanism of Tissue Fusion in Argon Laser–Welded Vein–Artery Anastomoses", Lasers in Surgery and Medicine, 1988 8:83–9.

* cited by examiner

VASCULAR SEALING DEVICE WITH MICROWAVE ANTENNA

RELATIONSHIP TO COPENDING APPLICATION

This application is a divisional of U.S. application Ser. No. 09/334,300, filed Jun. 16, 1999, (now abandoned) which is a continuation of U.S. application Ser. No. 08/963,408, filed Nov. 3, 1997, now U.S. Pat. No. 6,033,401, which is a continuation-in-part of Provisional U.S. Application Ser. No. 60/036,299, filed Mar. 12, 1997, entitled "Universal Introducer," which is a continuation-in-part of U.S. application Ser. No. 08/963,033, filed Nov. 3, 1997, (now abandoned) entitled "Vascular Sealing Device," which is a continuation-in-part of U.S. patent application Ser. No. 08/963,082, filed Nov. 3, 1997, (now abandoned) entitled "In Situ Formed Non-Fluent Closure Composition," all of which are incorporated by reference.

FIELD OF THE INVENTION

This invention relates to a vessel closure device, and more particularly to a device for effecting the closure of a vessel by delivering a fluent closure composition precursor and converting the composition in situ to a non-fluent closure composition.

BACKGROUND OF THE INVENTION

A wide variety of surgical procedures are performed by the introduction of a catheter into a vessel. After the surgical procedure is completed, closure of the vessel at the site where the catheter was introduced is needed. Vessel punctures formed in the process of performing a catheter based surgical procedure are commonly 1.5 mm to 7.0 mm in diameter and can be larger. Closure of these punctures is frequently complicated by anticoagulation medicine given to the patient which interferes with the body's natural clotting abilities.

Closure of a vessel puncture has traditionally been performed by applying pressure to the vessel adjacent the puncture site. This procedure requires the continuous attention of at least one medical staff member to apply pressure to the vessel puncture site and can take as long as 30 minutes.

Devices have been developed for effecting the closure of vessel punctures through the application of energy. See U.S. Pat. Nos. 5,626,601; 5,507,744; 5,415,657; and 5,002,051. Devices have also been developed for effecting the closure of vessel punctures through the delivery of a mechanical mechanism which mechanically seals the puncture. See U.S. Pat. Nos.: 5,441,520; 5,441,517; 5,306,254; 5,282,827; and 5,222,974. Devices have also been developed for effecting the closure of vessel punctures through the delivery of a composition to block the vessel puncture. See U.S. Pat. Nos. 5,601,602; 5,591,205; 5,441,517; 5,292,332; 5,275,616; 5,192,300; and 5,156,613. Despite the various devices that have been developed for closing vessel punctures, a need still exists for a simple, safe and inexpensive device and method for closing vessel punctures.

SUMMARY OF THE INVENTION

The present invention relates to a device and method for sealing a puncture in a body vessel. In one embodiment, the device has an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; and at least one position sensing mechanism positioned distal relative to the exit port such that the exit port is outside the vessel when the at least one position sensing mechanism is detected to be outside the vessel.

The closure device of this embodiment may optionally further include an energy delivery device for delivering energy adjacent the distal end of the elongated body to the fluent closure compound precursor. In one variation, the device includes a microwave antenna for delivering microwave energy adjacent the distal end of the elongated body to the fluent closure compound precursor. In another variation, the device includes a waveguide for delivering light energy adjacent the distal end of the elongated body to the fluent closure compound precursor. In yet another variation, the device includes a RF electrode for delivering RF energy adjacent the distal end of the elongated body to the fluent closure compound precursor.

In another embodiment, the device includes an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; and a microwave antenna for delivering microwave energy adjacent the distal end of the elongated body to the fluent closure compound precursor. The microwave antenna according to this embodiment is preferably incorporated onto the elongated body adjacent the body distal end.

In another embodiment, the device includes an elongated body having a proximal end and a distal end sized to be positioned within a lumen of the body vessel; at least one closure composition precursor lumen within the elongated body having a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture; a guidewire lumen within the elongated body; and a guidewire including microwave antenna for delivering microwave energy adjacent the distal end of the elongated body to the fluent closure compound precursor.

The present invention also relates to a method for sealing a puncture in a body vessel. In one embodiment, the method includes the steps of delivering a distal end of an elongated body into a lumen of the body vessel, the elongated body having at least one closure composition precursor lumen with a entrance port adjacent the proximal end of the elongated body through which one or more fluent closure composition precursors can be delivered into the closure composition precursor lumen and an exit port adjacent the distal end of the elongated body through which the one or more fluent closure composition precursors can be delivered outside the vessel adjacent the vessel puncture, and at least one position sensing mechanism positioned distal relative to the exit port such that the exit port is outside the vessel when the at least one position sensing mechanism is detected to be outside the vessel; withdrawing the elongated body until the at least one position sensing mechanism is positioned outside the vessel lumen; delivering one or more fluent closure composition precursors outside the vessel adjacent the vessel puncture; and transforming the one or more fluent closure composition precursors into a non-fluent closure composition which seals the vessel puncture.

In one variation, the method further includes the step of delivering energy adjacent the distal end of the elongated body to the fluent closure compound precursor to transform the one or more fluent closure composition precursors into the non-fluent closure composition. The energy may be microwave energy and the at least one of the one or more fluent closure composition precursors may optionally include a microwave energy absorbing material.

The present invention also relates to a non-fluent closure composition for closing a puncture in a vessel. In one embodiment, the non-fluent closure composition is formed by delivering a fluent closure composition precursor to a position outside the vessel adjacent to the puncture; and transforming the fluent closure composition precursor in situ to a non-fluent closure composition. In another embodiment, the non-fluent closure composition is formed by delivering two or more fluent closure composition precursors to a position outside the vessel adjacent to the puncture; and mixing the two or more fluent closure composition precursors to form a non-fluent closure composition in situ adjacent the vessel puncture.

Transforming the fluent closure composition precursor in situ may include solidifying the closure composition precursor or causing the closure composition precursor to chemically react with itself to form a non-fluent composition, the chemical reaction optionally being catalyzed by a catalyst or by energy. Energy used in the method may be any form of energy including, for example, RF energy and microwave energy. When microwave energy is used, the closure composition precursor includes a microwave energy absorbing material.

DETAILED DESCRIPTION OF THE PREFERRED EMBODIMENT

Figures 1A, 1B:
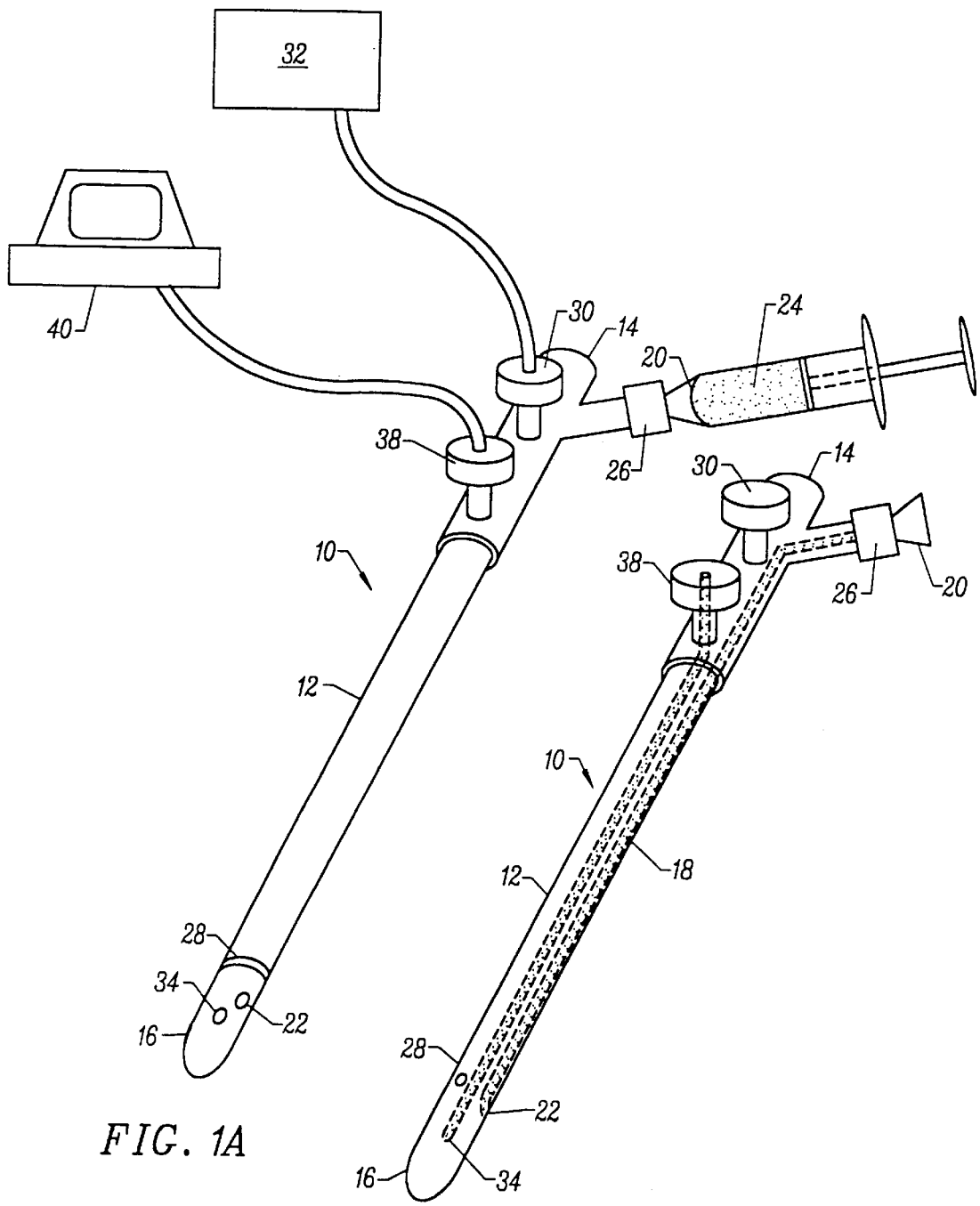
FIG. 1A is a sideview of a closure device according to the present invention.
FIG. 1B is a cross section of the closure device of FIG. 1A.

FIGS. 1A and 1B illustrate a closure device 10 according to the present invention. The closure device 10 may be used to seal a puncture in a vessel such as a femoral artery.

The closure device 10 includes an elongated body 12 with a proximal end 14 and a distal end 16 sized to be inserted into a lumen of a vessel. The surface of the elongated body 12 is preferably made of a non-stick material, such as Teflon, or coated with a biocompatible lubricant. Positioned within the elongated body 12 are one or more closure lumens which extend from adjacent the proximal end 14 of the device to the distal end 16 of the device for introducing a closure composition precursor adjacent the vessel puncture site. Illustrated in FIGS. 1A and 1B is a closure device 10 with a single closure lumen 18 with a precursor entrance port 20 and at least one precursor exit port 22 adjacent the distal end 16. The precursor entrance port 20 is preferably removably coupleable to a closure composition precursor source 24 for supplying the closure composition precursor to the closure device 10. The closure lumen 18 may optionally contain an anti-backflow valve 26 to prevent blood from flowing into the closure lumen 18 from the vessel.

The closure composition precursor can be formed of one or more fluent materials that can be flowed from the closure composition precursor source 24 to adjacent the device distal end 16 through the closure lumen 18. The fluent closure composition precursor is transformed into a non-fluent closure composition in situ to effect closure of the puncture. In a preferred embodiment, energy is applied to the closure composition precursor to accelerate its transformation into the non-fluent closure composition. The transformation of the fluent precursor to a non-fluent closure composition may be the result of a phase change (i.e. solidification) of the precursor or a chemical modification of the precursor. For example, the precursor may be formed from multiple components which react with each other, optionally accelerated by a catalyst or energy. Alternatively, the precursor may be formed from a single component which reacts with itself, also optionally accelerated by a catalyst or energy.

In embodiments where energy is applied, the body 12 includes an energy delivery device 28 adjacent the distal end 16. The energy delivery device 28 may be designed to deliver one or more different types of energy including but not limited to electromagnetic radiation (RF, microwave, ultraviolet, visible light, laser), ultrasound, resistive heating, exothermic chemical heating, and frictional heating. The energy source may also function to withdraw energy, i.e., perform cooling. The closure device 10 may also include an energy source attachment mechanism 30 for placing the energy delivery device 28 in energetic communication with an energy source 32.

The body 12 further includes at least one position sensing mechanism 34 adjacent the distal end 16 of the closure device 10 for indicating whether the position sensing mechanism 34 is located within or outside of the vessel 36. The position sensing mechanism 34 should be positioned on the body 12 distal to the precursor exit port 22 so that when the position sensing mechanism 34 is outside the vessel 36 the precursor exit port 22 is also outside the vessel 36. FIG. 1A illustrates the closure device 10 with a single position sensing mechanism 34. As illustrated, the closure device 10 may also include a position monitor attachment port 38 for coupling the position sensing mechanism 34 to a position monitor 40. Examples of a position sensing mechanisms include, but are not limited to, a pressure port and an electrical contact switch.

Other sensors (not shown) may also be positioned on the body 12. For instance, a temperature sensor for measuring temperature adjacent the distal end 16 of the body 12 and/or an impedance sensor may be positioned at the distal end 16 of the closure device 10.

Figure 2:
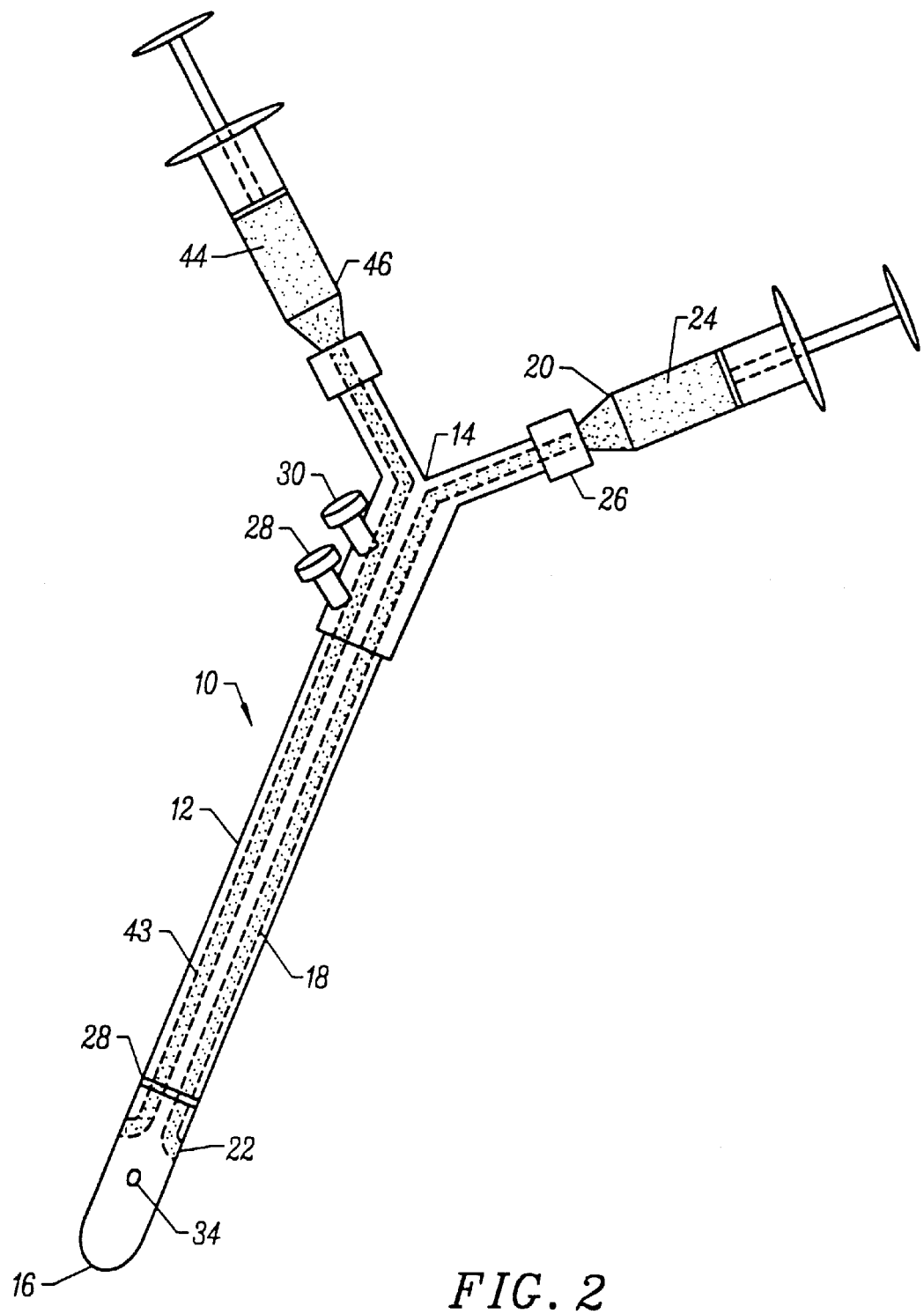
FIG. 2 is a cross section of a closure device with a first and second closure lumen coupled to first and second closure composition precursor sources.

The body 12 can include two or more closure lumens for the introduction of closure composition precursor. For example, as illustrated in FIG. 2, a second closure lumen 42 may be coupled to a second closure composition precursor source 44 by a second precursor entrance port 46. The second closure lumen 42 may also contain an anti-backflow valve 26 to prevent blood flow through the second closure lumen 42.

The closure composition precursor may be introduced adjacent the vessel puncture as a single composition through a single closure lumen. Alternately, a first composition may be introduced through the closure lumen 18 and a second composition can be introduced through the second closure lumen 42, as illustrated in FIG. 2. The first and second compositions can be the same or different and can be introduced simultaneously or at different times. The first and second compositions may interact to accelerate the transformation to the non-fluent closure composition at the tissue site 54, for example, by reacting with each other or by one catalyzing the solidification of the other.

Figures 3A, 3B:
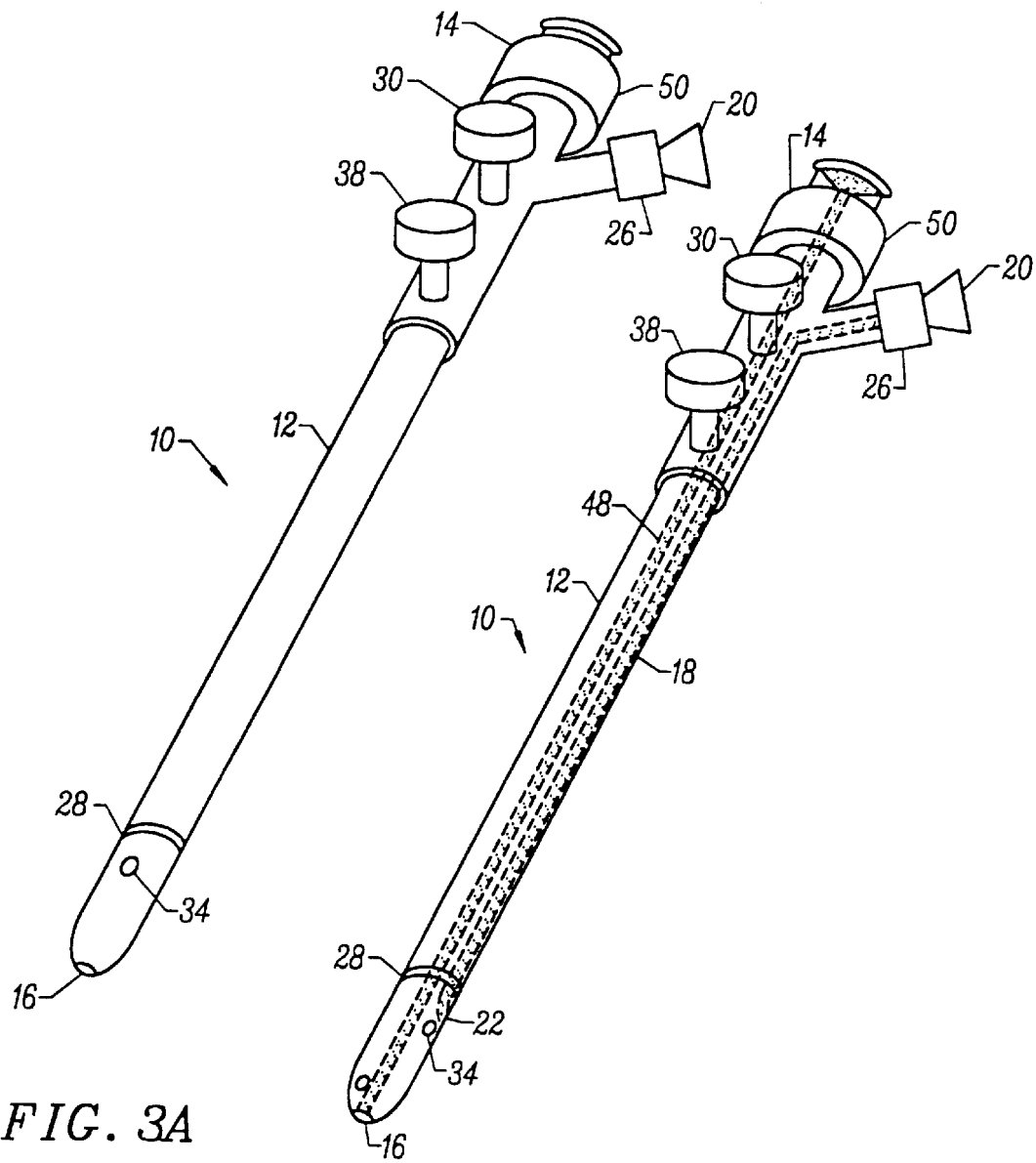
FIG. 3A is a sideview of a closure device including a guidewire lumen configured to accommodate a guidewire.
FIG. 3B is a cross section of a closure device illustrated in FIG. 3A.

FIGS. 3A–3B illustrate another embodiment of the invention configured to be used with a guidewire. As illustrated in FIG. 3A, the body 12 can include a guidewire lumen 48 configured to accommodate a guidewire. The guidewire lumen 48 can include an anti-backflow valve or hemostasis valve 50. FIG. 3B illustrates a cross-section of the device illustrated in FIG. 3B.

Figure 4A:
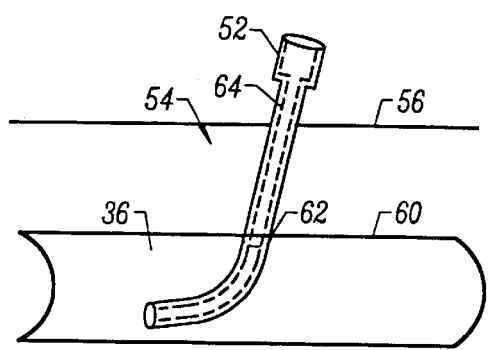
FIG. 4A illustrates a sheath with a distal end disposed within a vessel.

FIGS. 4A–4F illustrate a method of using the closure device 10 illustrated in FIGS. 1A–1B. The closure device 10 is used after a surgical procedure where a vessel 36 such as a femoral artery has been punctured. Angioplasty is a typical surgery which results in puncturing the femoral artery with a catheter. After the catheter devices from such a surgical procedure have been removed, a sheath 52 typically remains within a tissue site 54 as illustrated in FIG. 4A. The sheath 52 penetrates the skin 56 of the patient and passes through the underlying tissue to a vessel 60. The distal end 16 of the sheath 52 is positioned through a puncture 62 in the vessel 60.

Figure 4B:
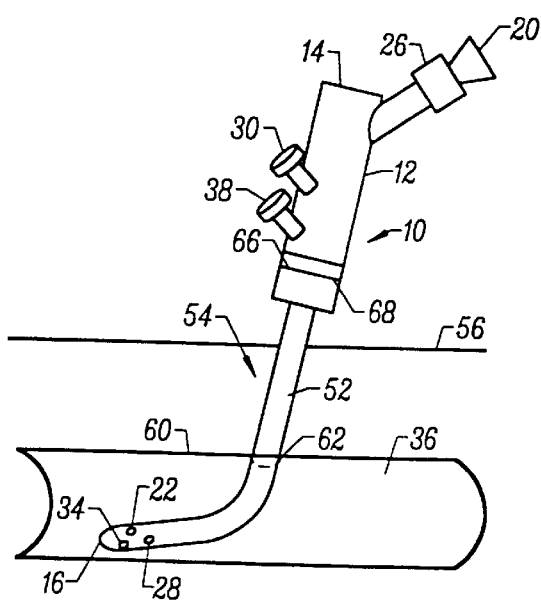
FIG. 4B illustrates a closure device disposed within the sheath such that the distal end of the closure device extends beyond the distal end of the sheath.

As illustrated in FIG. 4B, the closure device 10 is inser into the sheath lumen 64. The position of the closure device 10 within the sheath 52 may be set by fixing the closure device 10 to the sheath. For example, as illustrated, the closure device 10 may include a stop collar 66 which may engage an upper flange 68 on the sheath 64. The distal end 16 of the closure device 10 extends from the sheath 52 such that the position sensor 30 and precursor exit port 22 are distal relative to the sheath 52 and positioned within the vessel 60.

Figure 4C:
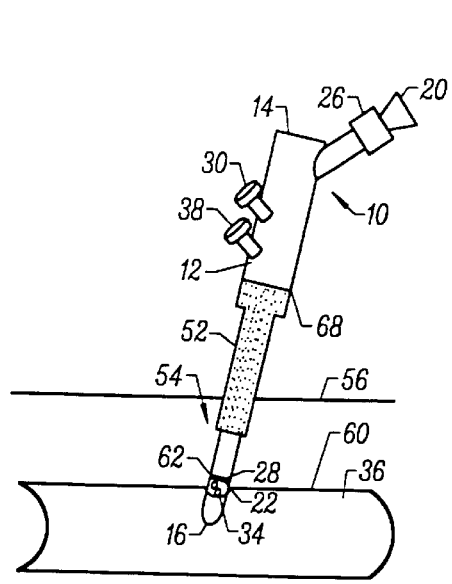
FIG. 4C illustrates the sheath and closure device withdrawn from the vessel until the position sensing mechanism is located outside the vessel adjacent the puncture.

As illustrated in FIG. 4C, the sheath 52 and closure device 10 are simultaneously withdrawn until the position sensor 30 is sensed to be located outside the vessel 60. Since the precursor exit port 22 is positioned distal relative to the position sensor 30, the precursor exit port 22 is necessarily positioned outside the vessel 60 when the position sensor is outside the vessel 60.

Figure 4D:
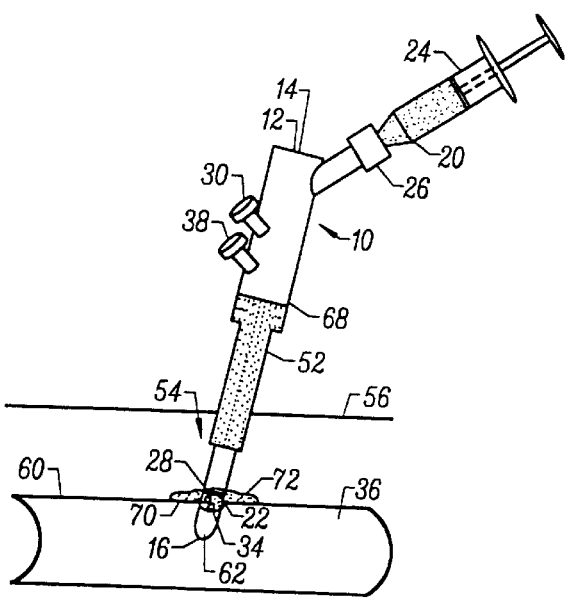
FIG. 4D illustrates a closure composition precursor source coupled to the closure device of FIG. 4C. The closure composition precursor is delivered through the closure lumen to the puncture.

As illustrated in FIG. 4D, a fluent closure composition precursor 70 is delivered through the closure lumen 18 and out the precursor exit port 22 after the precursor exit port 22 is determined to be outside the vessel 60. The fluent closure composition precursor 44 should have sufficiently low viscosity to allow the closure composition precursor to flow through the closure lumen 18. Once delivered, the closure composition precursor 44 accumulates adjacent the vessel 60. The transformation of the closure composition precursor to a non-fluent closure composition serves to seal the vessel puncture 62. Energy can optionally be delivered from the energy delivery device 28 to the closure composition precursor as illustrated by arrows 72 in order to cause and/or accelerate transformation to the non-fluent closure composition. Alternatively or in addition, a catalyst can be added to catalyze the conversion of the fluent precursor to a non-fluent closure composition.

Figure 4E:
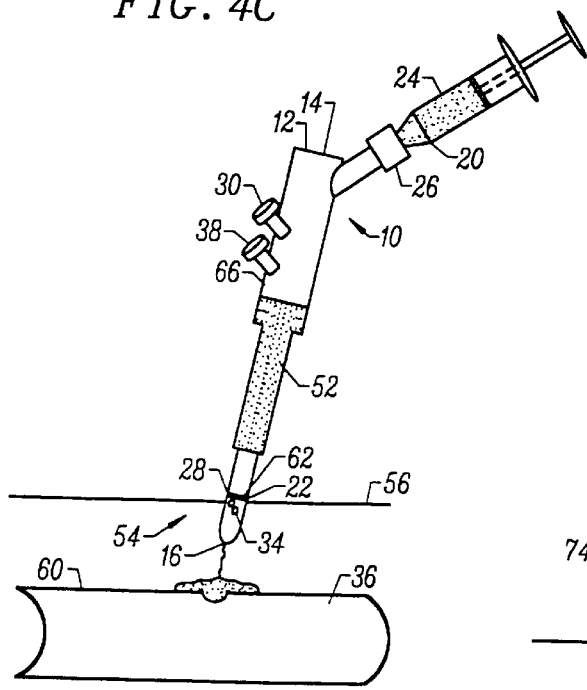
FIG. 4E illustrates the puncture after the closure device of FIG. 4D is withdrawn from the puncture.

FIG. 4E illustrates the withdrawal of the closure device 10.

Figure 4F:
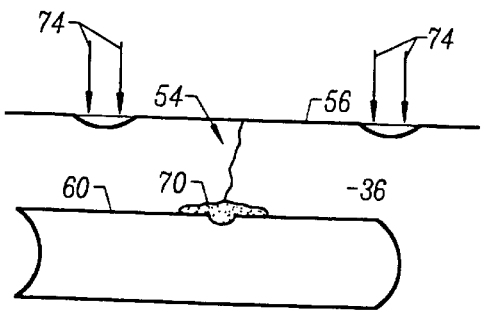
FIG. 4F illustrates the puncture after the closure device is completely withdrawn from the tissue site.

In FIG. 4F the closure device 10 is completely withdrawn from the tissue site 54 and pressure is being applied at the arrows 74 for a sufficient period of time after the closure composition precursor is delivered to allow the closure composition to transition to non-fluent closure composition.

Figures 5A, 5B:
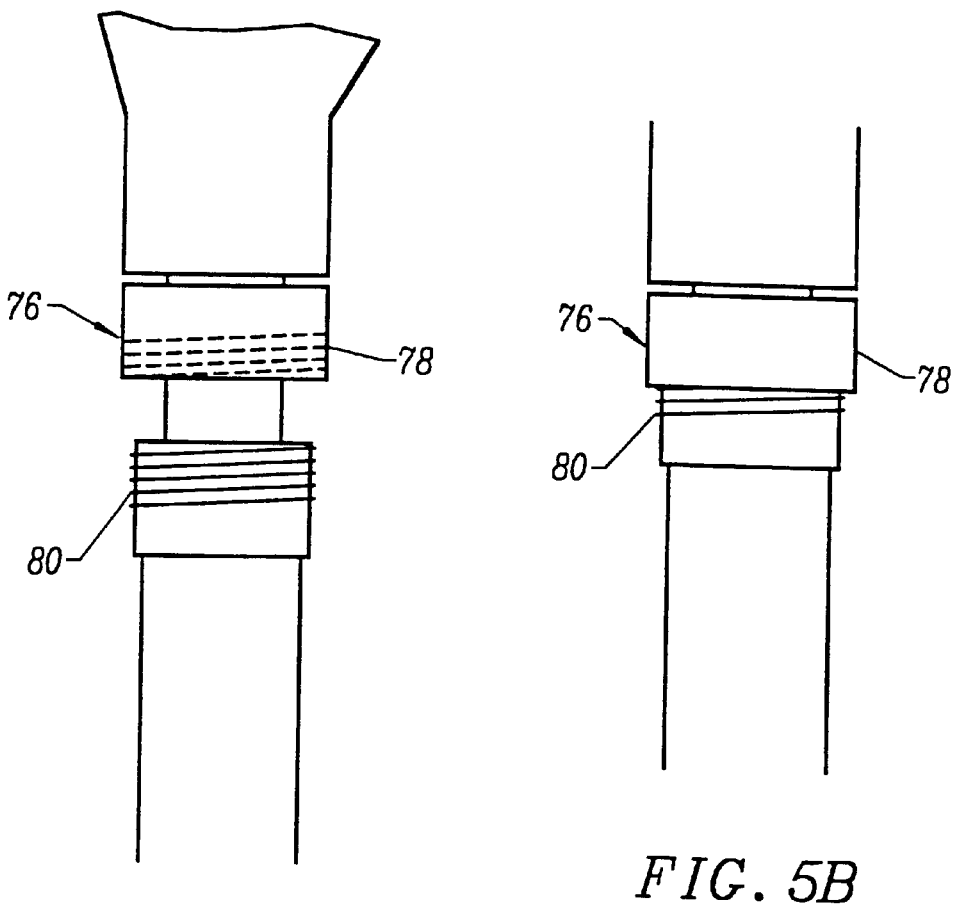
FIG. 5A is a sideview of a locking mechanism coupled to a closure device and threads on a sheath.
FIG. 5B is a sideview of the locking mechanism of FIG. 5A coupled to the threads on a sheath.

The body 12 can optionally further include a locking mechanism 76 for coupling the closure device 10 to the sheath 52. For example, as illustrated in FIGS. 5A and 5B, the locking mechanism 76 can be a threaded nut 78 complementary to threads 80 at the proximal end 14 of the sheath 52. When the closure device 10 is positioned within the sheath 52 the threaded nut 78 is turned to engage the threads 80 on the sheath 52 as illustrated in FIG. 5B. As a result, the sheath 52 and closure device 10 move as a unitary body. Movement as a unitary body is desirable to prevent the closure device 10 from moving relative to the sheath 52 when the closure device 10 is withdrawn from the tissue site 54. Other mechanisms can be used to lock the closure device to a sheath including, for example, straps, snap-fit arrangements, bayonet locks, magnets, adhesives, and detents.

Figure 6A:
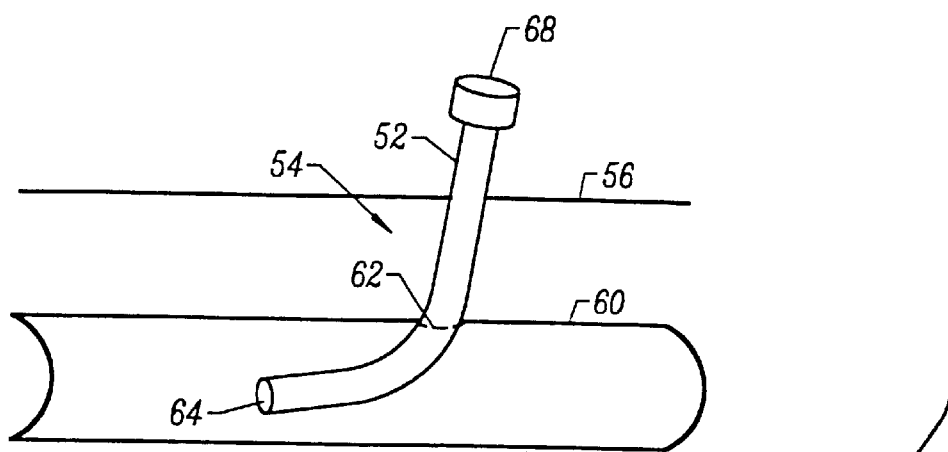
FIG. 6A illustrates a sheath with a distal end disposed within a vessel.

FIGS. 6A–6G illustrate a method of using the closure device 10 illustrated in FIGS. 3A–3B which include a guidewire. As discussed with regard to the method illustrated by FIGS. 4A–4F, the method makes use of a sheath 52 left in place after a surgical procedure. FIG. 6A illustrates the sheath 52 in place in a tissue site 54 after the surgical procedure.

Figure 6B:
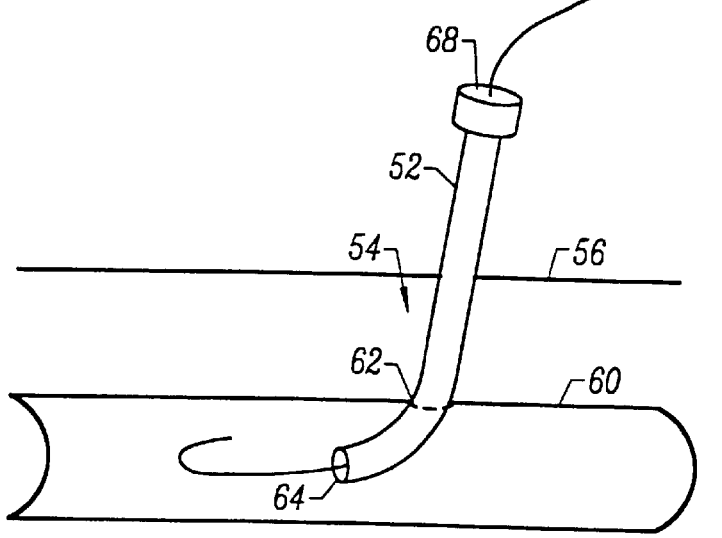
FIG. 6B illustrates a guidewire disposed within the sheath of FIG. 6A.

As illustrated in FIG. 6B a guidewire 82 is inserted into the vessel 60 through the sheath lumen 64.

Figure 6C:
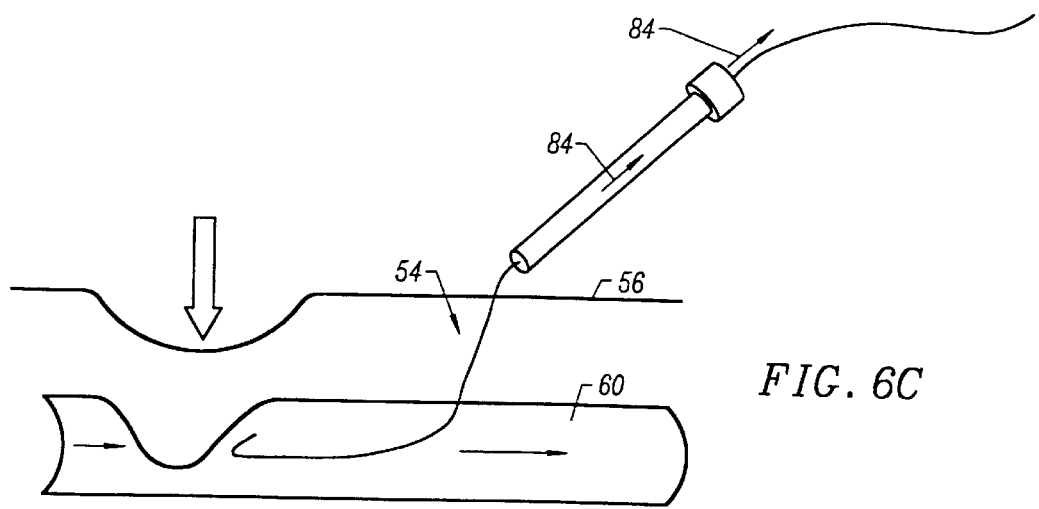
FIG. 6C illustrates the sheath of FIG. 6B withdrawn along the guidewire.

Pressure is applied to the skin 56 upstream from the puncture 62 as shown by arrow 76 in FIG. 6C to prevent bloodflow through the vessel 60. The sheath 52 is then withdrawn from the tissue site 54 along the guidewire 82 as illustrated by arrow 84.

Figure 6D:
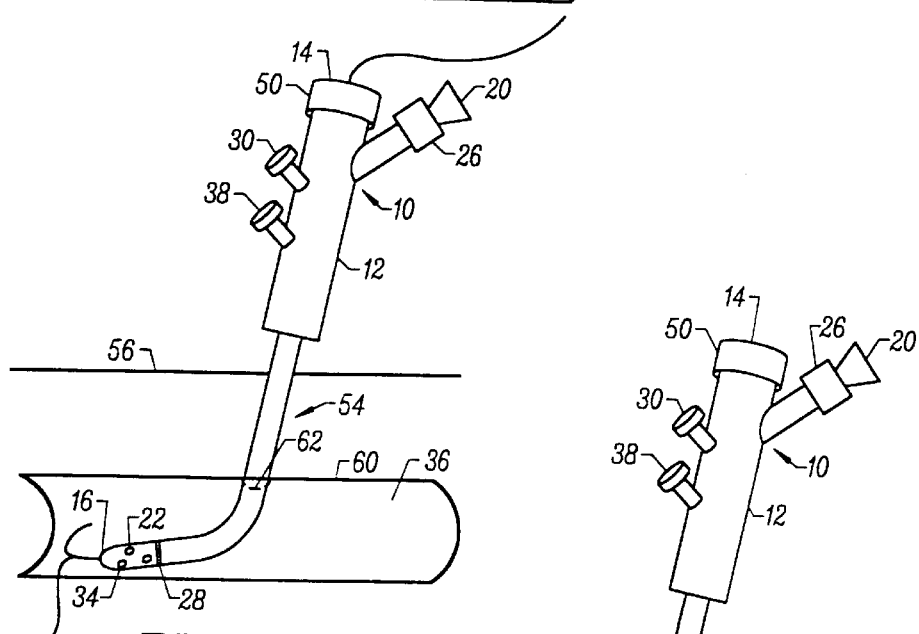
FIG. 6D illustrates a closure device threaded along the guidewire of FIG. 6C until the distal end of the device is disposed within a vessel.

As illustrated in FIG. 6D, the guidewire 82 is then thread within the guidewire lumen 48 of the closure device 10 and the distal end 16 is pushed forward through the tissue site 54 until the position sensor 30 indicates that the position sensor 30 is within the vessel 60. The distal end 16 of the closure device 10 preferably has the same or larger diameter as the sheath used in the surgical procedure. Since the puncture 62 has been dilated to the diameter of the sheath 52, this sizing reduces leakage of blood between the puncture 62 and the closure device 10.

Figure 6E:
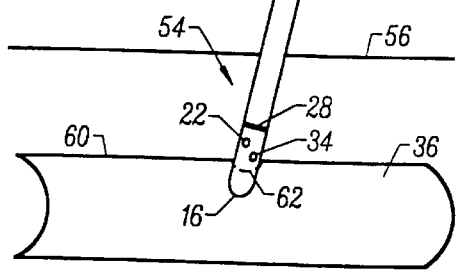
FIG. 6E illustrates the closure device of FIG. 6D after the guidewire has been withdrawn. The closure device is withdrawn until the position sensing mechanism is located outside the vessel adjacent the puncture.

As illustrated in FIG. 6E, the closure device 10 is slowly withdrawn from the vessel 60 until the position sensor 30 indicates that the position sensor 30 is located outside the vessel 60. Since the precursor exit port 22 is positioned proximally relative to the position sensor 30, withdrawal of the position sensor from the vessel 60 assures that the precursor exit port 22 has been withdrawn from the vessel 60.

Figure 6F:
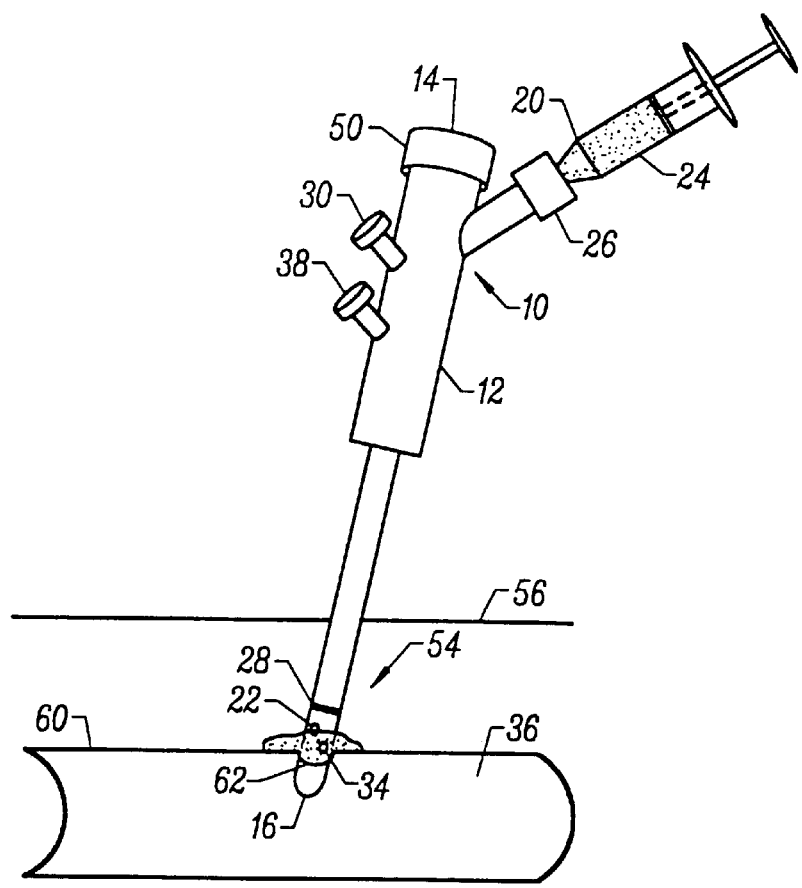
FIG. 6F illustrates a closure composition precursor source coupled to the closure device of FIG. 6E. The closure composition precursor is delivered through the closure lumen to the puncture.

As illustrated in FIG. 6F, once the precursor exit port 22 is determined to be outside the vessel 60, a closure composition precursor 44 is delivered through the closure lumen 18 and out the precursor exit port 22 adjacent the vessel puncture 62.

Figure 6G:
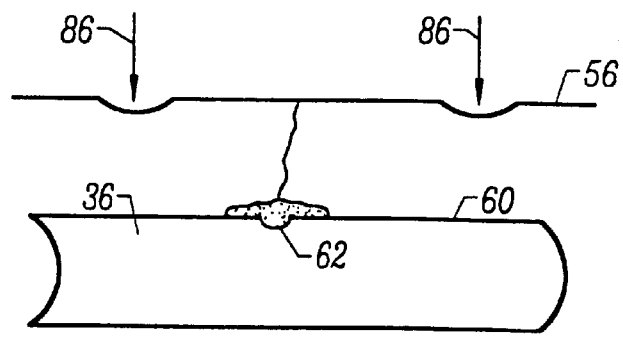
FIG. 6G illustrates the puncture after the closure device is completely withdrawn from the tissue site.

FIG. 6G illustrates the complete withdrawal of the closure device 10 from the tissue site 54. Pressure is applied at the arrows 86 until desired transformation of the fluent closure composition precursor to the non-fluent closure composition is substantially completed.

The energy delivery device 28 can be optionally used to deliver a form of energy which functions to accelerate the transformation of the fluent closure composition precursor to non-fluent closure composition. Alternatively or in addition, a catalyst can be added to catalyze the conversion of the fluent precursor to a non-fluent closure composition. Most commonly, energy is used to increase the temperature of the closure composition precursor. In one embodiment, the energy delivery device 28 is a microwave antenna positioned on or within the body 12. The guidewire 82 can also include a microwave antenna. When microwave energy is employed, the closure composition precursor preferably includes materials capable of absorbing microwave energy. Examples of such materials include, but are not limited to, hematite ($\alpha$-$Fe_2O_3$), maghemite (y-$Fe_2O_3$), magnetite ($Fe_3O_4$), geothite ($\alpha$-FeOOH), lepidocrocite (y-FeOOH), ferrihydrite, feroxyhyte ($\delta$-FeOOH), akageneite ($\beta$-FeOOH) graphite and amorphous carbon.

Figures 7A, 7B:
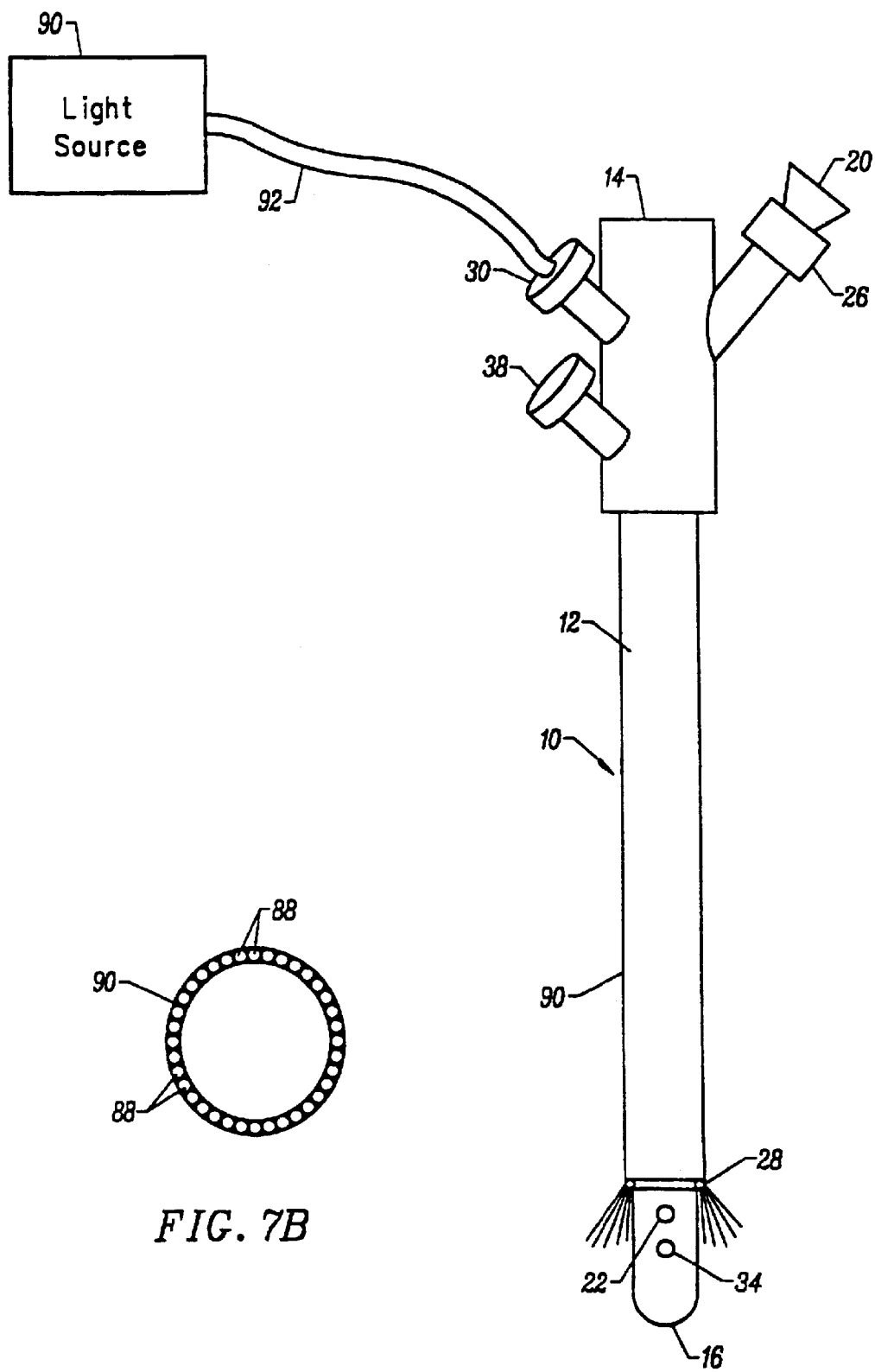
FIG. 7A is a sideview of a closure device including a fiber optic ring as a energy delivery device.
FIG. 7B is a cross section of the fiber optic ring of FIG. 7A.

The energy delivery device 28 may also be a wave guide 88 for delivery of UV, visible light or laser energy as illustrated in FIG. 7A. The closure device 10 includes a waveguide collar 90. FIG. 7B illustrates a cross section of the waveguide collar 90. A plurality of waveguides 88 are arranged circumferentially around the collar. The light is provided to the waveguides 88 through a cable 92 coupled to a light source 94.

The energy delivery device 28 may also be an electrode for delivering RF energy. The electrode can be a ring electrode encircling the body 12 as illustrated in FIG. 1A or a more localized electrode as illustrated in FIG. 2. The RF supply wires are run through the body 12 and coupled to the energy source attachment port 30. Alternatively, RF energy may be delivered to the closure composition precursor via the guidewire 82. Other types of energy 10 can also be used, including those that deliver ultrasound, resistive heating, exothermic chemical heating, other forms of electromagnetic radiation, and frictional heating.

Referring again to FIG. 1A, one example of a position sensing mechanism 34 is a pressure port coupled to the position monitor attachment port 38 by a position lumen. The position monitor 40 is a pressure sensor coupled to the position sensor attachment port by tubing. As a result, an open channel is created between the pressure port and the pressure sensor allowing the pressure sensor to detect the pressure at the port. The pressure within the vessel 60 is elevated compared with the pressure in the surrounding tissue. As a result, the signal from the pressure sensor indicates whether the position port is located within or outside the vessel 60.

Figures 8A, 8B:
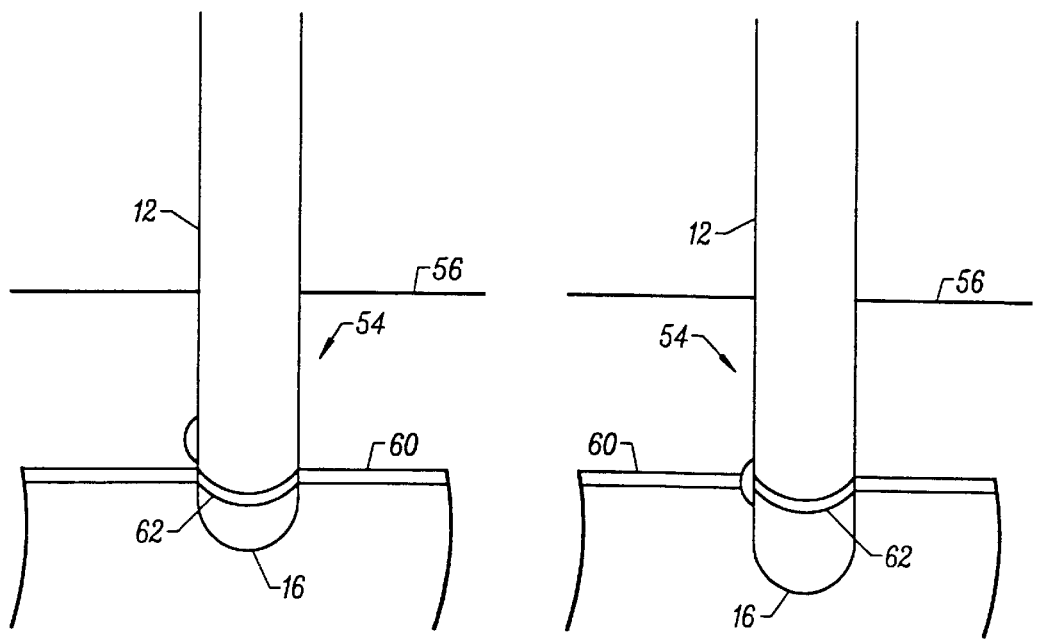
FIG. 8A is a sideview of a closure device with a contact switch as a position sensing mechanism.
FIG. 8B is a sideview of a contact switch of FIG. 8A being compressed by the vessel wall.

The position sensing mechanism 34 can also be a contact switch 96 as illustrated in FIGS. 8A and 8B. The contact switch is coupled to the position monitor attachment port 38 by wires run through the body (not shown). When the switch 96 is in contact with the vessel wall the switch 96 closes and a circuit (not shown) is completed, however, when the switch 96 is not in contact with the vessel wall, the switch 96 remains open and the circuit is not completed. The circuit is monitored to determine the position of the closure device 10 relative to the vessel 60. Alternatively, the circuit can be coupled to the energy delivery device 24 such that the energy cannot be delivered unless the circuit is completed. In one embodiment, the device includes a mechanism which prevents the closure composition from being delivered if the position sensor is sensed to be within the vessel. As a result, energy will not be delivered unless the closure device 10 is properly positioned within the tissue site 54.

Figures 9A, 9B:
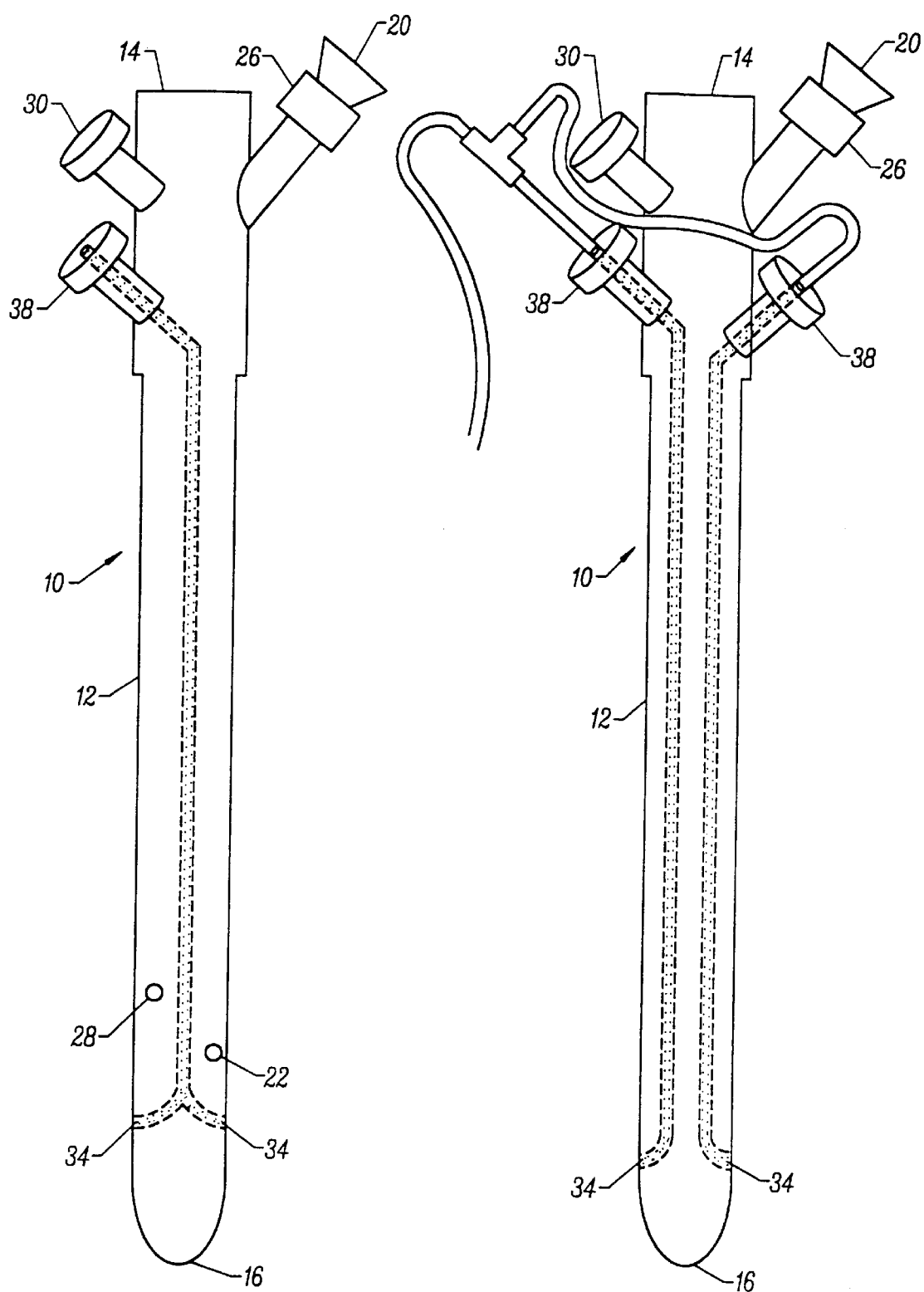
FIG. 9A is a cross section of a closure device containing a plurality of precursor exit ports coupled to a single closure lumen.
FIG. 9B is a cross section of a closure device containing a plurality of precursor exit ports coupled to a plurality of closure lumens.

In a preferred embodiment, the closure device 10 includes two or more position sensors positioned around the closure device 10 where a reading that the sensor is outside the vessel occurs when all of the sensors are outside of the vessel. By having more than one position sensor around the closure device 10, false readings from one of the position sensors are reduced or avoided. For instance, if a single position sensing mechanism 34 is used, the sensing mechanism may become pressed against the vessel wall resulting in a pressure drop at the position sensing mechanism 34. The position monitor 40 would falsely provide a signal indicating that the position sensing mechanism 34 is outside the vessel 60. When a second position sensing mechanism is included, the second position sensing mechanism would still be exposed to the pressure within the vessel 60. As a result, the position monitor 40 would not provide a false signal. FIGS. 9A and 9B illustrate a closure device 10 with two position sensing mechanisms. In FIG. 9A, two pressure ports are coupled to a single position lumen. In FIG. 9B, each pressure port is coupled to a separate position lumen but both position lumens are coupled to the same tubing before the tubing is coupled to the pressure sensor.

Figure 9C:
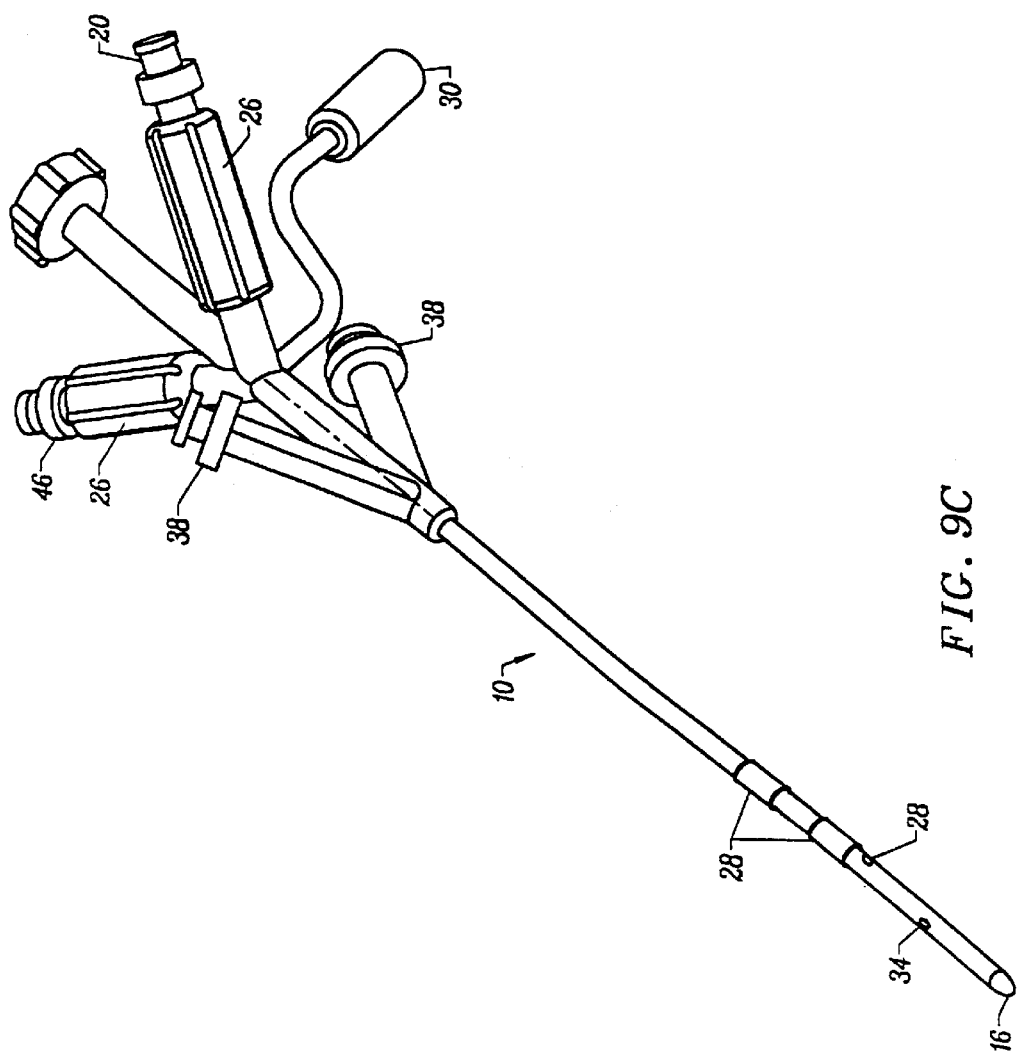
FIG. 9C illustrates a closure device with a plurality of pressure ports and first and second closure lumens.

FIG. 9C illustrates another embodiment of the closure device 10 according to the present invention. The closure device 10 includes a plurality of pressure ports 34 and a first closure closure compoistion port 20 and a second precursor entrance port 46. An energy delivery port 30 is coupled to a plurality of energy delivery devices 28. The closure device 10 includes a guidewire lumen 48 for use with the method described in FIG. 6A–6G.

When the position sensing mechanism 34 is a contact switch or a pressure port, the position sensing mechanism 34 is preferably positioned at least 25 mm from the distal end 16. This positioning assures that the distal end 16 of the closure device 10 remains within the vessel 60 when the closure device is positioned to deliver the closure composition precursor. This feature reduces the risk of delivering the closure composition precursor to an improper location on the vessel or within the vessel.

Figures 10A, 10B:
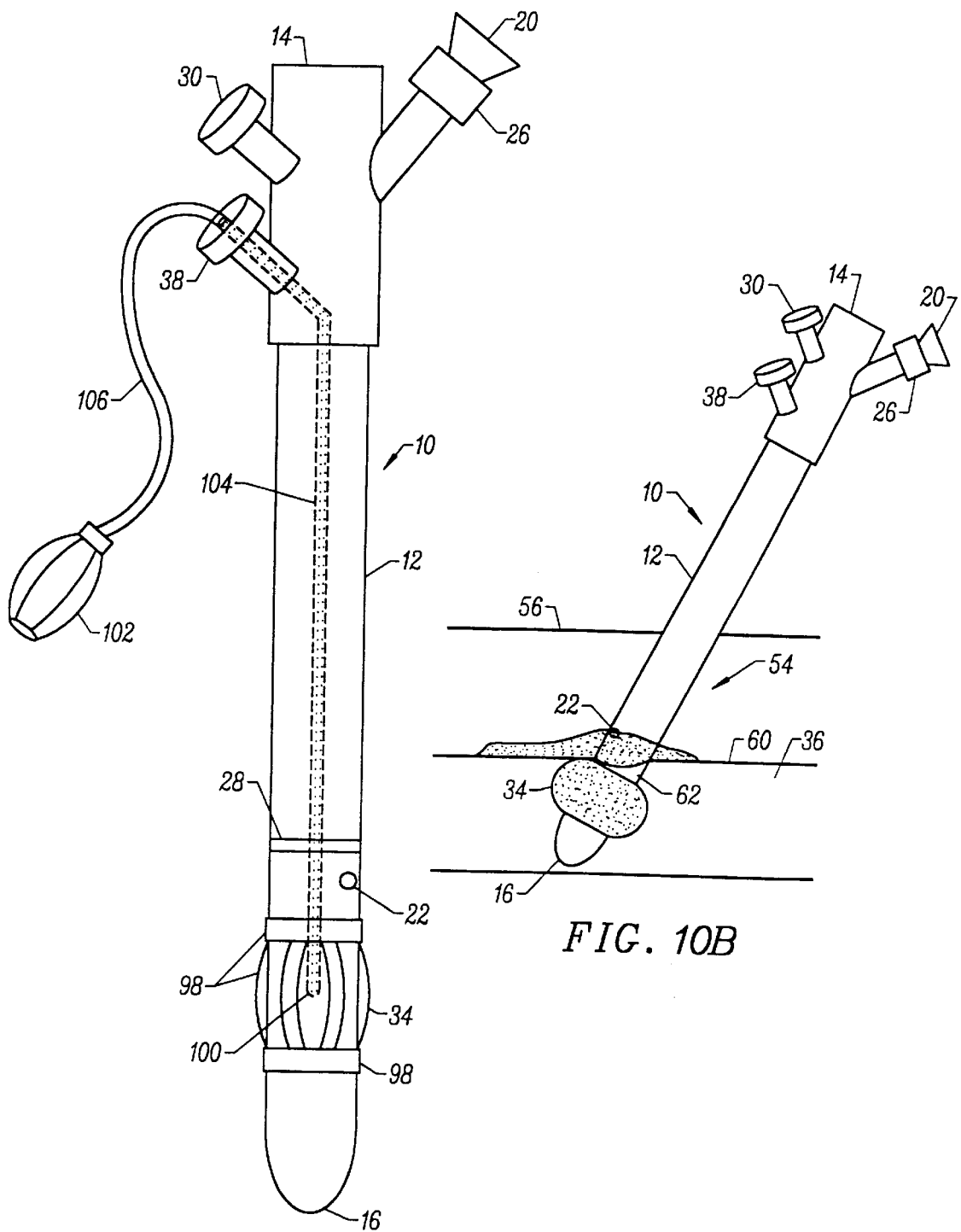
FIG. 10A is a sideview of a closure device including a balloon as the position sensing device.
FIG. 10B illustrates the closure device of FIG. 10A disposed within a vessel.

FIGS. 10A and 10B illustrate another position sensing mechanism 34. A balloon 98 is coupled to the distal end 16 of the closure device 10 by a first and second retaining collar 99. The balloon is positioned over an inflation port 100. The balloon is coupled to an inflation bulb 102 by an inflation lumen 104 and an inflation tube 106. The balloon 98 is deflated when the closure device 10 is positioned within the vessel 60. Once the balloon 98 enters the vessel 60, the balloon 98 is inflated to a diameter greater than the diameter of the sheath 52 and thus the puncture 62. The closure device 10 is then withdrawn until the resistance of the balloon against the puncture 62 is felt as illustrated in FIG. 10B. The resistance indicates that the precursor exit port 22 is outside the vessel 60 and properly positioned for application of the closure composition precursor.

Figure 11:
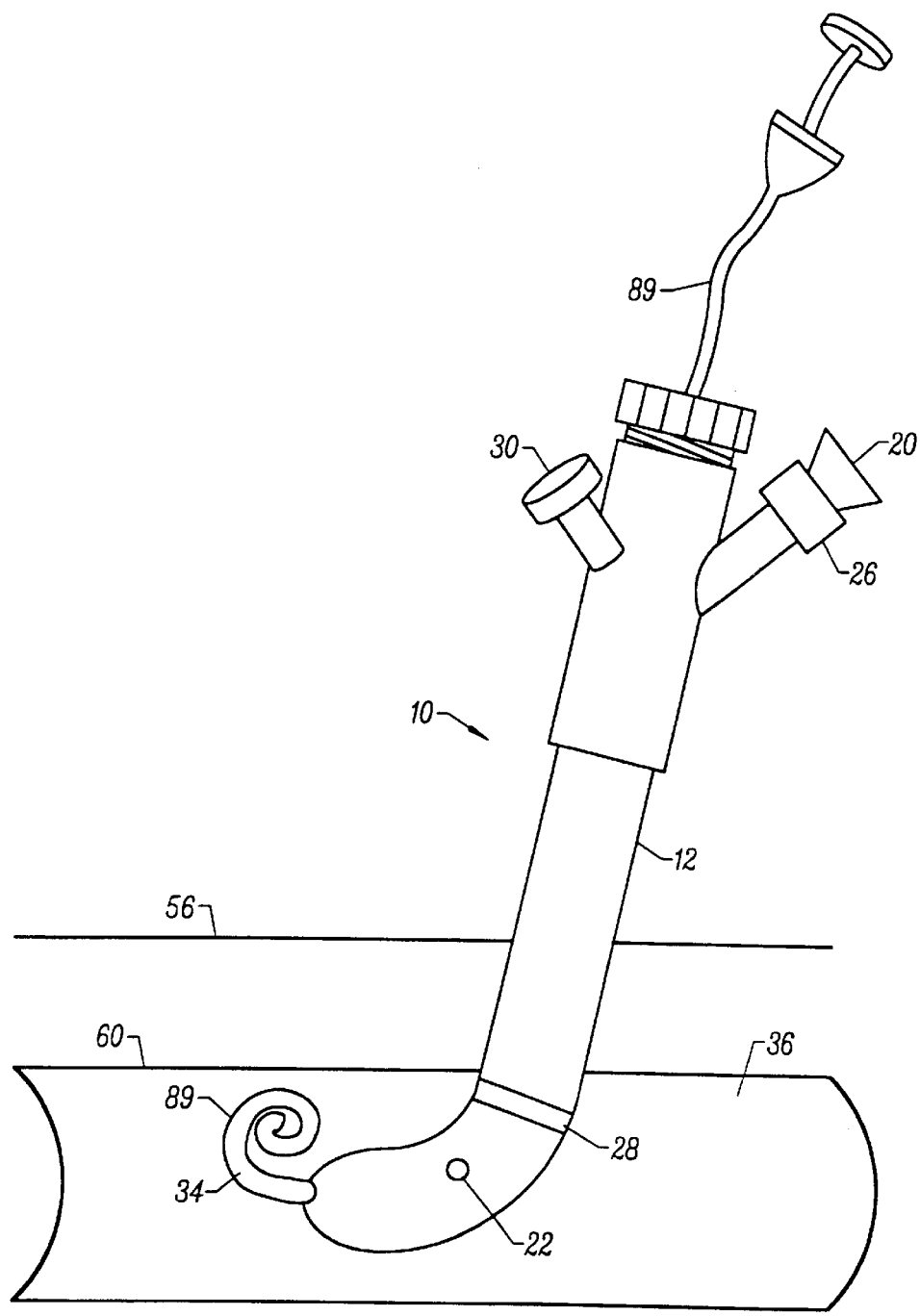
FIG. 11 illustrates a position sensing mechanism in the form of a curved wire positioned within the vessel lumen.

FIG. 11 illustrates yet another embodiment of a position sensing mechanism 34. According to this embodiment, a curved wire 89 is positioned within the vessel. As the vessel is withdrawn, resistance is felt when the curved wire is pushed up against the interior of the vessel lumen. The closure precomposition ports are positioned such that when the resistance is felt, the precomposition ports are known to be positioned outside of the vessel.

Each position sensing mechanism 34 can be distally positioned 0.5–30 mm from the precursor exit port 22 and more preferably 3.0–9.0 mm from the precursor exit port 22. These distances allow the closure composition precursor to be reliably delivered outside the vessel 60 once the closure device 10 is positioned for delivery of the closure composition precursor.

A variety of additional sensors may be used in combination with the present invention. For example, temperature sensors may be positioned adjacent the distal end 16 of the closure device 10 for detecting the temperature adjacent the distal end 16. The temperature sensors may be a thermocouple positioned on the surface of the body 12 (not shown) and hardwired to electrical contacts within a sensor monitor attachment port (not shown). These sensors are useful for regulating the amount of energy being delivered to the vessel 60 and tissue adjacent the closure device 10 and for preventing tissue damage and ablation due to excess heat application.

Impedance sensors may also be employed when RF is used in order to monitor the amount of energy being delivered to the tissue.

Figures 12A, 12B:
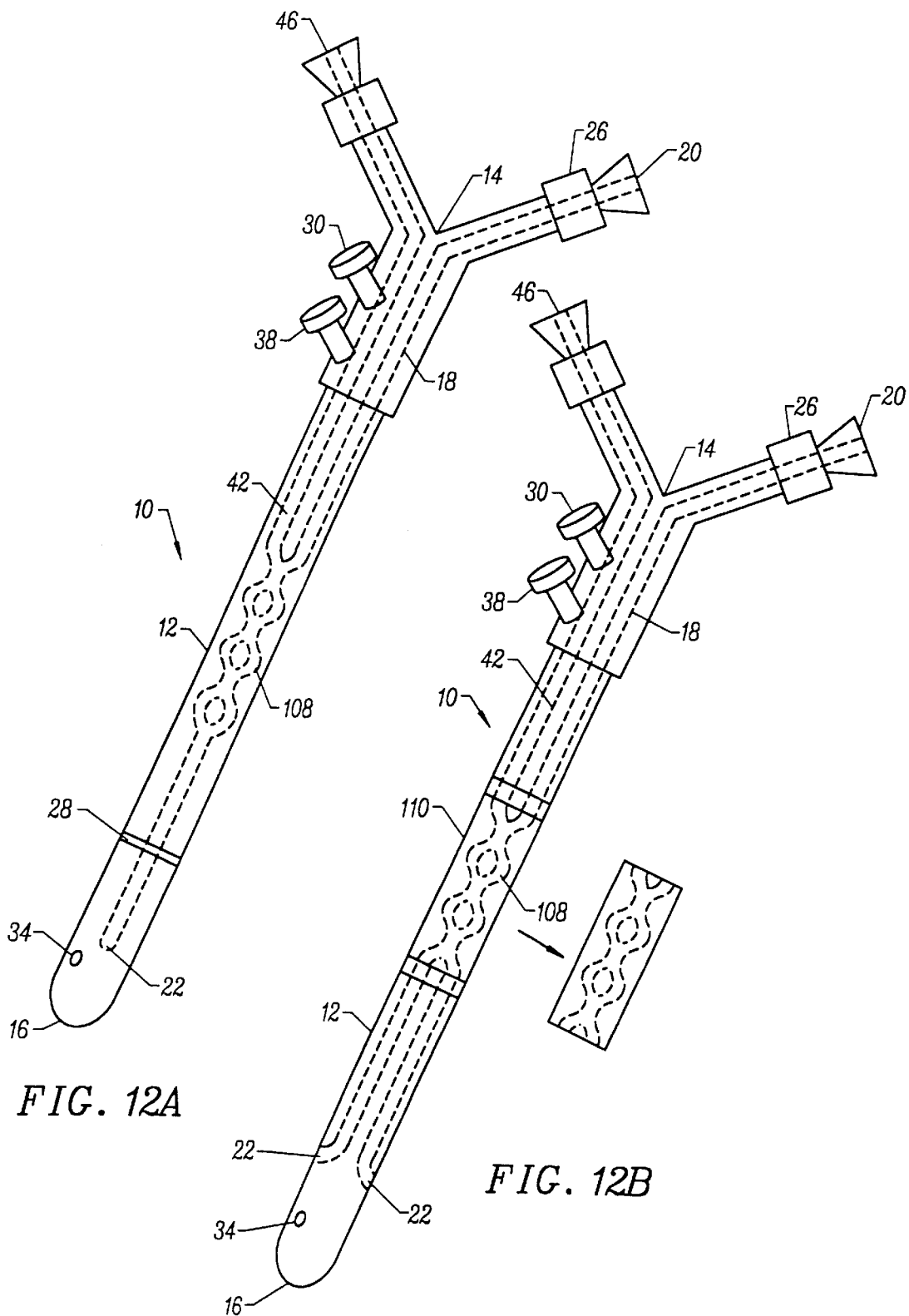
FIG. 12A is a cross section of a closure device with a plurality of closure lumens and a static mixer.
FIG. 12B is a cross section of a static mixer which is a removable cartridge.

When the closure composition precursor is formed of two or more components, the closure device 10 can optionally include a static mixer 108 for mixing different closure composition precursor components before the closure composition precursors exit the precursor exit port or ports 22. FIG. 12A illustrates a static mixer 108 incorporated into the closure device 10. The first closure lumen 18 and the second closure lumen 42 intersect at least one time before terminating in at least one precursor exit port 22. The static mixer can also be a cartridge 110 incorporated into the body 12 of the closure device 10 as illustrated in FIG. 12B. The intersection of the first and second lumens assures that the first and second closure composition precursors are mixed before reaching the at least one precursor exit port 22.

Figure 13:
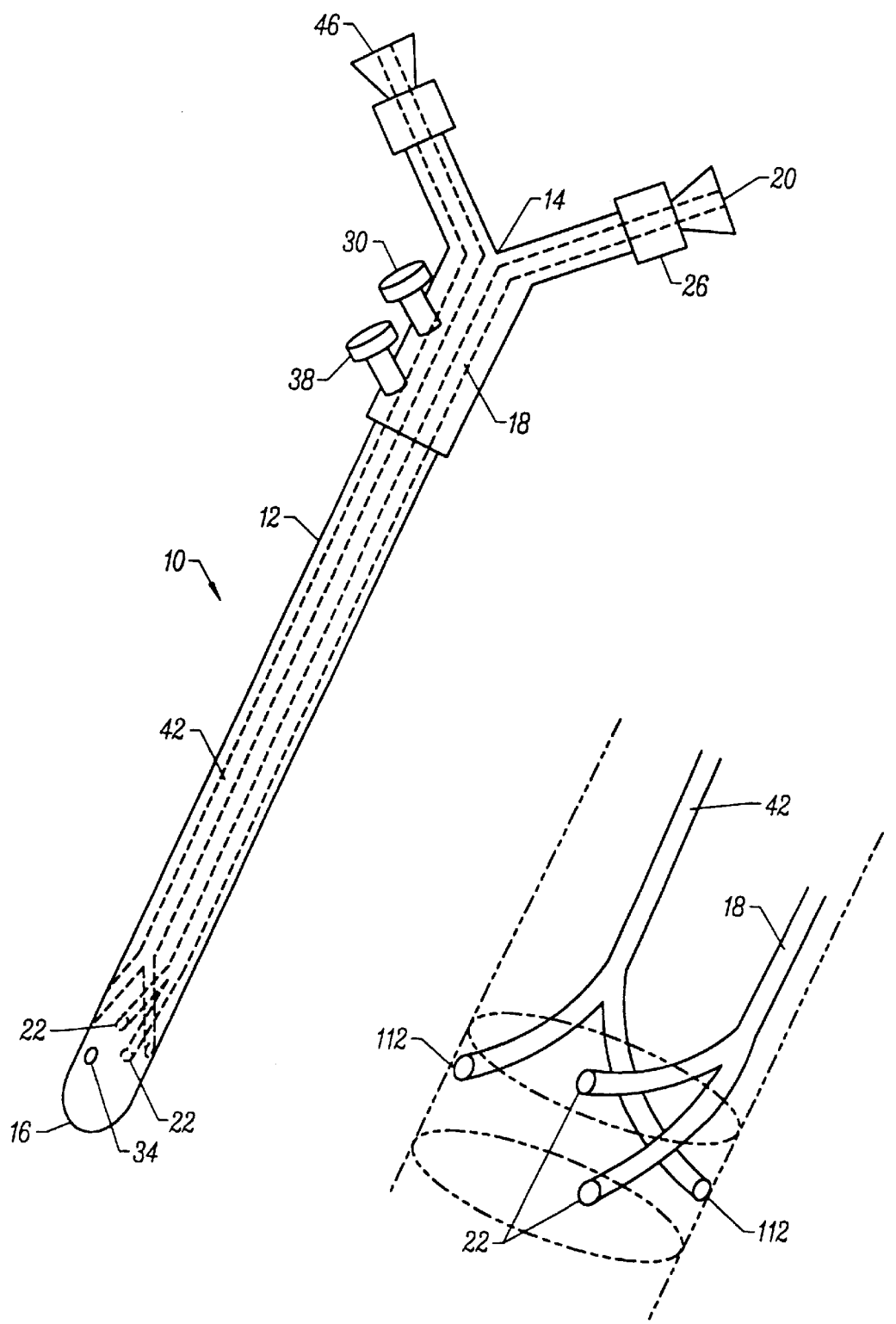
FIG. 13 is a cross section of a closure device which alternate the precursor exit ports from a first closure compound with the precursor exit ports of a second closure compound.

The configuration of precursor exit ports can also serve to assure adequate mixing of the first and second closure composition precursors. As illustrated in FIG. 13, the precursor exit ports 22 corresponding to the first closure composition alternate with the precursor exit ports corresponding with the second closure composition 112. As a result, the first and second closure composition precursors are mixed outside the closure device 10.

Figures 14A, 14B:
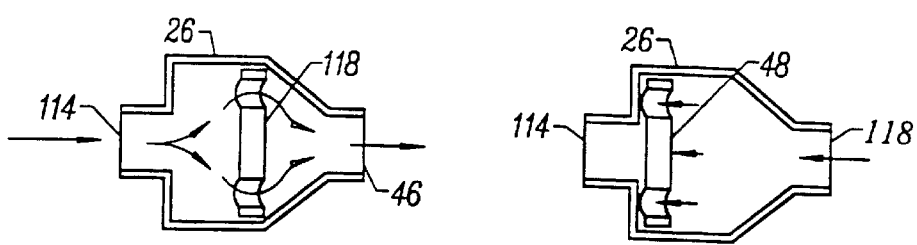
FIG. 14A is a cross section of an anti-backflow valve.
FIG. 14B is a cross section of an anti-backflow valve.

A backflow valve 26 which is suitable for use in a closure lumen is illustrated in FIGS. 14A and 14B. The valve 26 has a composition entrance 114 and a composition exit 116. FIG. 14A illustrates that when a fluid flows from the entrance 114 to the exit 116, a diaphragm 118 slides forward to allow the closure composition precursor to flow freely through the valve 26. FIG. 14B illustrates that when a fluid flows from the exit 116 to the entrance 114, the fluid places pressure against the backside of the diaphragm 118 causing the diaphragm 118 to slide against the entrance 114 sealing the entrance 114 and preventing a flow of fluid through the valve 26.

Figures 15A, 15B:
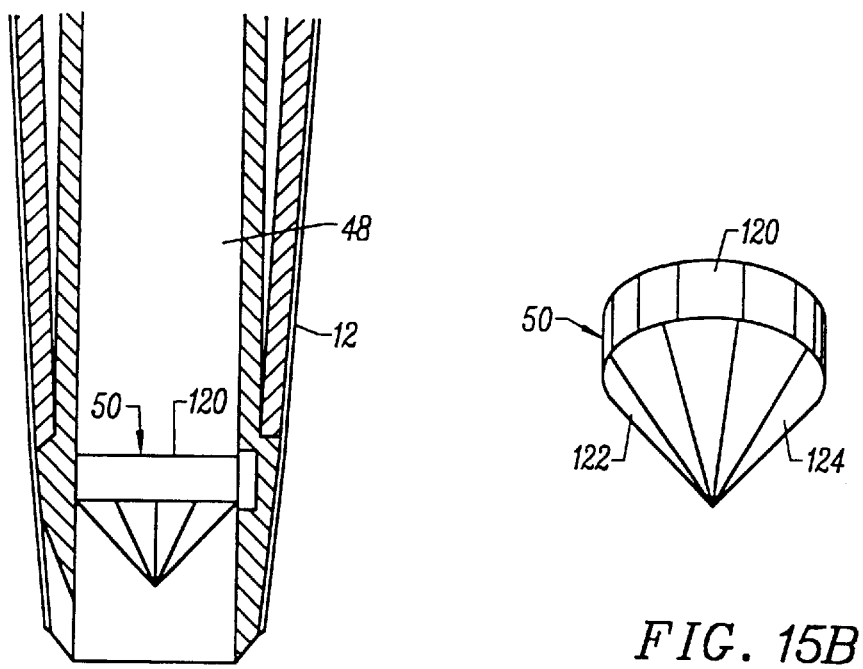
FIG. 15A illustrates a flapper valve disposed within the distal end of a closure device.
FIG. 15B is a sideview of a flapper valve.

An example of a suitable backflow valve 50 for use in the central lumen 48 adjacent the distal end of the device is a flapper valve 120 as illustrated in FIGS. 15A and 15B. Examples of backflow valves for the central lumen which may be positioned adjacent the proximal end of the device include, but are not limited to, duckbill valves, hemostasis valves, and Tuhoy-Bourse valves. The flapper valve 120 is preferably formed of an elastomeric material such as medical grade silicone rubber. The configuration, as illustrated by FIG. 15B, may be a cylindrical section transitioning into a conical portion. The conical portion has a series of slits 122 which allow various implements to pass through the valve 50. The thickness of the flaps 124 and the flexibility of the elastomeric material will be balanced to provide memory sufficient to close the puncture as the implements are withdrawn and provide a fluid seal. Blood pressure against the outer surface of the cone will cause the flapper valve 50 to close more tightly.

The body 12 is formed of any suitable, relatively flexible material. Suitable materials include, but are not limited to, polyethylene, PEBAX polytetrafluroethylene (TEFLON) and polyurethane.

A variety of different closure composition precursors and non-fluent closure compositions can be used in the present invention. The fluent closure composition precursor and non-fluent closure composition should be biocompatible and preferably bioresorbable. The closure composition should be also capable of forming a strong puncture seal and be able to seal larger sized vessel punctures, e.g., punctures formed by 8 french or larger needles. Examples of closure compositions that can be used with the device and method of the present include, but are not limited to sealants and adhesives produced by Protein Polymer Technology (Ethicon); FOCALSEAL produced by Focal; BERIPLAST produced by Centeon (JV Behringwerke & Armour); VIVOSTAT produced by ConvaTec (Bristol-Meyers-Squibb); SEALAGEN produced by Baxter; FIBRX produced by CyoLife; TISSEEL AND TISSUCOL produced by immuno AG; QUIXIL produced by Omrix Biopharm; a PEG-collagen conjugate produced by Cohesion (Collagen); HYS-TOACRYL BLUE produced by Davis & Geck; NEXACRY, NEXABOND, NEXABOND S/C, and TRAUMASEAL produced by Closure Medical (TriPoint Medical); OCTYL CNA produced by Dermabond (Ethicon); TISSUEGLU produced by Medi-West Pharma; and VETBOND produced by 3M. Examples of two part closure compositions which may be used are listed in Table 1.

| CLASS OF ADHESIVE | PART A | PART B |
|---|---|---|
| (Meth) Acrylic (redox initiated) | (Meth) acrylic functional monomers and oligomers with oxidant initator | (Meth) acrylic functional monomers and oligomers with reductant initator |
| Polyurethane | Poly isocyanate | Hydrocarbon polyol, polyether polyol, polyester polyol |
| Polyurea | Poly isocyanate | Hydrocarbon polyamine, polyether polyamine |
| Ionomer | Polyvalent metal cation | Acrylic acid (co) polymer, alginate |
| Epoxy | Epoxy resin | Aliphatic polyamine, catalyst |

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. An assembly for introducing a closure material to seal a vessel puncture site, the closure material comprising a mixture of a first and second fluid composition which, upon mixing, react to form a nonfluent closure composition, the assembly comprising a catheter for passage through a tissue puncture and having a distal end, at least one fluid delivery port adjacent the catheter distal end to occupy a position adjacent the vessel puncture site, and a lumen in the catheter in fluid communication with the fluid delivery port, one or more dispensers in fluid communication with the catheter lumen for dispensing the first and second fluid compositions in the catheter lumen, and an actuator for causing the first and second fluid compositions to be dispensed from the one or more dispensers mixed by flowing the first and second fluid compositions through a static mixer within the lumen and dispensed from the fluid delivery port as a fluid mixture that reacts in situ to form the nonfluent closure composition adjacent the vessel puncture site, wherein the catheter is sized to block flow of the fluid mixture from the fluid delivery port into a substantial part of the tissue puncture, whereby a localized in situ closure forms adjacent the vessel puncture site to seal the vessel puncture site.

2. An assembly as in claim 1, wherein the static mixer is incorporated into the catheter.

3. An assembly as in claim 1, wherein the static mixer is a cartridge.

4. A method for sealing a vascular puncture site comprising the steps of introducing a catheter through a tissue puncture, the catheter including a distal end and at least one fluid delivery port adjacent the distal end to be positioned adjacent the vessel puncture site, the catheter being sized to occupy substantially all the tissue puncture, providing first and second fluid compositions which, upon mixing, react to form a nonfluent closure composition, mixing the first and second fluid compositions by flowing the components through a lumen containing a static mixer in the catheter, the lumen communicating with the fluid delivery port, and dispensing the first and second fluid compositions from the fluid delivery port as a fluid mixture that reacts in situ to form the nonfluent closure composition adjacent the vessel puncture site, the size of the catheter blocking flow of the fluid mixture from the fluid delivery port into a substantial part of the tissue puncture, whereby a localized in situ closure forms adjacent the vessel puncture site seal the vessel puncture site.

5. A method as in claim 4 wherein the static mixer is incorporated into the catheter.

6. A method as in claim 4, wherein the static mixer is a cartridge.

* * * * *